(12) United States Patent
Naddaka et al.

(10) Patent No.: US 7,659,398 B2
(45) Date of Patent: Feb. 9, 2010

(54) IMIQUIMOD PRODUCTION PROCESS

(75) Inventors: Vladimir Naddaka, Petach Tikva (IL); Shady Saeed, Haifa (IL); Stephen Cherkez, Caesarea (IL); Oded Arad, Rehovot (IL)

(73) Assignee: Chemagis Ltd., Bnei Brak (IL)

( * ) Notice: Subject to any disclaimer, the term of this patent is extended or adjusted under 35 U.S.C. 154(b) by 501 days.

(21) Appl. No.: 11/675,024

(22) Filed: Feb. 14, 2007

(65) Prior Publication Data

US 2008/0194822 A1 Aug. 14, 2008

(51) Int. Cl.
*C07D 471/12* (2006.01)
(52) U.S. Cl. ............................................. 546/82
(58) Field of Classification Search .................. 546/82
See application file for complete search history.

(56) References Cited

U.S. PATENT DOCUMENTS

| | | |
|---|---|---|
| 4,689,338 A | 8/1987 | Gerster |
| 4,929,624 A | 5/1990 | Gerster et al. |
| 4,988,815 A | 1/1991 | André et al. |
| 5,175,296 A | 12/1992 | Gerster |
| 5,367,076 A | 11/1994 | Gerster |
| 7,323,568 B2 | 1/2008 | Naddaka et al. |
| 2005/0085500 A1 | 4/2005 | Gutman et al. |
| 2006/0004202 A1 | 1/2006 | Razzetti et al. |
| 2007/0010675 A1 | 1/2007 | Allegrini et al. |
| 2007/0135640 A1 | 6/2007 | Naddaka et al. |
| 2008/0177074 A1 | 7/2008 | Naddaka et al. |

FOREIGN PATENT DOCUMENTS

| | | |
|---|---|---|
| EP | 1609792 A1 | 12/2005 |
| WO | WO 2005/033049 A2 | 4/2005 |
| WO | WO 2005/033049 A3 | 4/2005 |
| WO | WO 2006/070379 A1 | 7/2006 |
| WO | WO 2006/100226 A1 | 9/2006 |
| WO | WO 2008/090550 A2 | 7/2008 |
| WO | WO 2008/090550 A3 | 7/2008 |
| WO | WO 2008/099377 A2 | 8/2008 |
| WO | WO 2008/099377 A3 | 8/2008 |

OTHER PUBLICATIONS

Office Action dated Jun. 7, 2007 in U.S. Appl. No. 11/298,711.
Bredereck et al., "Umsetzungen von Halogenverbindungen mit Formamid (Formamid-Reaktionen), III. Mitteilung. II. Mitteil.: G. Theilig, Chem. Ber. 86, 96 [1953])," *Chemische Berichte*, 87(4), 537-546 (1954).
P. Jacobson, "Ueber die Einwirkung von Dinitrochlorbenzol auf Kaliumbenzoat und auf Acetamid," *Berichte der Deutschen Hemischen Gesellschaft*, 32, 3539-3540 (1899).
Pachter et al., "Methylation of Some Amides in Acetone," *J. Am. Chem. Soc.*, 74, 1321-1322 (1952).
Rondestvedt Jr. "Aminations With Ammonia and Formamide. Synthesis of Terephtalamic Acid and of p-Nitroaniline," *J. Org. Chem.*, 42(19), 3118-3123 (1977).
Sarges et al., "4-Amino[1,2,4]triazolo[4,3-a]quinoxalines. A novel class of potent adenosine receptor antagonists and potential rapid-onset antidepressants", J. Med Chem, vol. 33, No. 8, pp. 2240-2254 (Aug. 1990).

*Primary Examiner*—Taofiq A Solola
(74) *Attorney, Agent, or Firm*—Leydig, Voit & Mayer, Ltd.

(57) ABSTRACT

The present invention provides a process for preparing highly pure 4-amino-1-isobutyl-1H-imidazo[4,5-c]quinoline (imiquimod). The process preferably includes heating 4-chloro-1-isobutyl-1H-imidazo[4,5-c]quinoline of formula (II) with ammonia in a polar aprotic solvent at relatively moderate pressure to produce imiquimod, and optionally purifying the imiquimod. The process of the present invention can produce highly pure imiquimod in high yield.

18 Claims, No Drawings

IMIQUIMOD PRODUCTION PROCESS

BACKGROUND OF THE INVENTION 4-amino-1-isobutyl-1H-imidazo[4,5-c]quinoline, also known as imiquimod, is an immune response modifier, indicated for treating genital warts. Imiquimod is also indicated for topical treatment of clinically typical, nonhyperkeratotic, nonhypertrophic actinic keratoses on the face or scalp in immunocompetent adults and for the treatment of biopsy-confirmed, primary superficial basal cell carcinoma in immunocompetent adults, with a maximum tumor diameter of 2.0 cm, located on the trunk (excluding anogenital skin), neck, or extremities (excluding hands and feet).

The drug is marketed as a 5% cream under the trade name Aldara® and has the following structural formula (I):

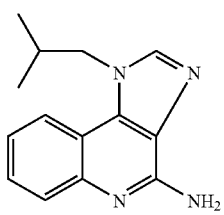

The synthesis of imiquimod was described in several patents, for example in U.S. Pat. Nos. 4,689,338 and 4,929,624 (to Minnesota Mining and Manufacturing Co. Inc.). The final step of the processes described therein involves an ammonolysis reaction carried out by heating the compound 4-chloro-1-isobutyl-1H-imidazo[4,5-c]quinoline of formula (II) in the presence of ammonium hydroxide or ammonia in methanol under high pressure (e.g. in a steel bomb) at 150° C. to afford imiquimod of formula (I), as depicted in Scheme 1.

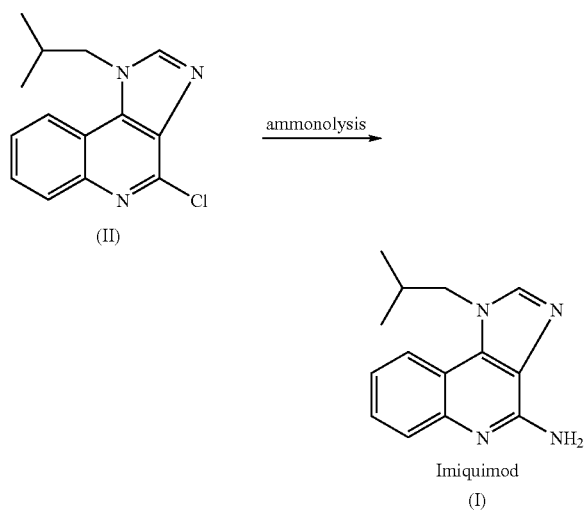

U.S. Pat. No. 4,988,815 describes another process for preparing imiquimod, wherein the final step similarly involves ammonolysis of the compound 4-chloro-1-isobutyl-1H-imidazo[4,5-c]quinoline. The ammonolysis reactions described in U.S. Pat. Nos. 4,689,338 and 4,929,624 are disadvantageous in that the reactions require high temperature and high pressure, which is undesirable from the standpoint of industrial safety.

WO 2006/070379 discloses yet another process for preparing imiquimod, wherein the compound 4-chloro-1-isobutyl-1H-imidazo[4,5-c]quinoline is converted to 4-iodo-1-isobutyl-1H-imidazo[4,5-c]quinoline by reacting it with sodium iodide in acetone followed by converting the 4-iodo-1-isobutyl-1H-imidazo[4,5-c]quinoline to imiquimod by using methanolic ammonia at a temperature of 150-155° C. and high pressure of about 20 bars.

US 2007/0010675 (hereinafter the '675 application) discloses a process for purifying imiquimod via its organic acid addition salts, e.g., the imiquimod formate salt. The '675 application states that "the processes used for imiquimod preparation usually do not provide highly pure imiquimod so that, for regulatory requirements to be fulfilled, imiquimod has to be subjected to a subsequent purification process."

Thus, there is a need in the art for an improved process for preparing highly pure imiquimod from 4-chloro-1-isobutyl-1H-imidazo[4,5-c]quinoline that will be more suitable for industrial use in comparison to conventional processes and will enable the preparation of highly pure imiquimod under more industrially feasible conditions. There is also a need for a simple, straightforward process for obtaining highly pure imiquimod. The present invention provides such a process.

BRIEF SUMMARY OF THE INVENTION

In one embodiment, the present invention provides a process for preparing highly pure 4-amino-1-isobutyl-1H-imidazo[4,5-c] quinoline (imiquimod) of formula (I), using gaseous ammonia at relatively moderate pressure, which process preferably includes:

admixing 4-chloro-1-isobutyl-1H-imidazo[4,5-c]-quinoline of formula (II) with a polar, aprotic solvent;

adding gaseous ammonia and heating to produce the compound of formula (I);

cooling the reaction mixture;

isolating the compound of formula (I); and optionally purifying the obtained compound of formula (I).

The compound of formula (I) can be purified by any suitable method, which can include, for example, precipitation, crystallization, slurrying, washing in a suitable solvent, filtration through a packed-bed column, dissolution in an appropriate solvent (e.g., dimethyl sulfoxide (DMSO)) and re-precipitation by addition of a second solvent in which the compound is insoluble, or any combination of such purification methods.

Preferably, the crude imiquimod is purified by a slurrying method, which includes:

suspending imiquimod in a solvent;

mixing optionally at elevated temperature;

optionally filtering the hot solution;

cooling for sufficient time to allow crystallization; and collecting the crystals by filtration, washing and drying.

The method of the present invention produces highly pure imiquimod, e.g., having a purity of at least 98.5%, a purity of at least about 99.5%, or a purity of at least about 99.8%.

DETAILED DESCRIPTION OF THE INVENTION

The present invention provides a simplified process for preparing highly pure 4-amino-1-isobutyl-1H-imidazo[4,5-c]quinoline (imiquimod) of formula (I), using gaseous ammonia at relatively moderate pressure.

The applicants have surprisingly discovered, that by dissolving the starting material 4-chloro-1-isobutyl-1H-imidazo[4,5-c]-quinoline of formula (II) in a polar, aprotic solvent, the ammonolysis reaction can be carried out at relatively moderate pressure to enable obtaining highly pure imiquimod in high yield. As utilized herein, the term "polar, aprotic solvent" refers to a solvent lacking an acidic hydrogen, and having sufficiently high dielectric constant and ion dissolving power to dissolve 4-chloro-1-isobutyl-1H-imidazo[4,5-c]-quinoline and/or imiquimod.

The process of the present invention preferably includes:
  admixing 4-chloro-1-isobutyl-1H-imidazo[4,5-c]-quinoline of formula (II) with a polar, aprotic solvent;
  adding gaseous ammonia and heating;
  cooling the reaction mixture;
  isolating the compound of formula (I); and
  optionally purifying the obtained compound of formula (I).

Suitable polar aprotic solvents can include dimethyl sulfoxide (DMSO), N-methyl-2-pyrrolidone (NMP), tetramethylene sulfone (sulfolane), hexamethylphosphorotriamide (HMPA), and mixtures thereof. In a particularly preferred embodiment, the polar aprotic solvent is dimethyl sulfoxide (DMSO), which has a high boiling point and is pharmaceutically acceptable solvent, and can be readily used on industrial scale because it is non-volatile and non-toxic. The use of DMSO also is advantageous because the starting material 4-chloro-1-isobutyl-1H-imidazo[4,5-c]-quinoline of formula (II) is very soluble in the solvent, which facilitates completion of the reaction.

Thus, in accordance with the present invention, the use of a polar, aprotic solvent, e.g., DMSO, enables the reaction to be carried out at relatively moderate pressure, e.g., about 5 bars or less.

The progress of the reaction can be monitored using any suitable method, which can include, for example, chromatographic methods such as, e.g., high performance liquid chromatography (HPLC), thin layer chromatography (TLC), and the like. The reaction may be stopped after nearly complete disappearance of the starting material 4-chloro-1-isobutyl-1H-imidazo[4,5-c]-quinoline as determined by one or more of such methods.

In one embodiment, at least about 2 equivalents of ammonia relative to one equivalent of the compound of formula (II) are used in the process, and the process is carried out at a temperature of from about 145° C. to about 150° C.

The imiquimod produced in accordance with the present invention can be isolated by any suitable method. In one embodiment, the imiquimod is isolated by cooling the reaction mixture, preferably after reaction completion, to precipitate imiquimod, and collecting the precipitate by filtration. The process of the present invention can produce crude imiquimod in high yield, which is preferably greater than 85% yield.

The crude imiquimod, e.g., as obtained by precipitation, can be washed with any suitable solvent, which can include, e.g., water, methanol, ethanol, 1-propanol, 2-propanol, or a mixture thereof. Preferred solvents for washing the crude imiquimod include water, methanol or a mixture thereof.

In accordance with the present invention, the purification of the crude compound of formula (I) can be carried out by any suitable method, which can include, e.g., precipitation, crystallization, slurrying, washing in a suitable solvent, filtration through a packed-bed column, dissolution in an appropriate solvent (e.g., dimethyl sulfoxide (DMSO)) and re-precipitation by addition of a second solvent in which the compound is insoluble, or any suitable combination of such methods. Preferably, the crude imiquimod is purified by slurrying the imiquimod in a solvent. In a preferred embodiment, the crude imiquimod is purified by a method that includes:
  suspending imiquimod in a solvent;
  mixing the suspension, optionally at elevated temperature, to dissolve at least a portion of the imiquimod;
  optionally filtering the solution, e.g., as a hot solution;
  cooling for sufficient time to allow crystallization;
  collecting the crystals by filtration; and
  optionally washing and drying the crystals.

The slurrying solvent preferably includes 1-propanol, 2-propanol, toluene, acetonitrile, acetone, ethyl acetate, tetrahydrofuran (THF), 2-methylterahydrofuran, or a mixture thereof. The imiquimod:slurrying solvent ratio is preferably at least about 1 g:1 mL (imiquimod:slurrying solvent), and more preferably is about 2 g:3-30 mL (imiquimod: slurrying solvent). Preferably, the solvent used for washing the crystals includes water, methanol, ethanol, 1-propanol, 2-propanol, or a mixture thereof. A preferred solvent for washing the crystals is methanol.

The process of the present invention provides highly pure imiquimod having a purity of at least about 98.5%, preferably having a purity of at least about 99.5%, and more preferably having of at least about 99.8%.

The following examples further illustrate the invention but, of course, should not be construed as in any way limiting its scope.

EXAMPLE 1

This example demonstrates the preparation of imiquimod by reaction of compound II with ammonia in DMSO at 140-150° C. under a pressure of about 5 bar.

A 250 glass reactor "Miniclave" was charged with 4-chloro-1-isobutyl-1H-imidazo [4,5-c]quinoline (II) (20 g, 0.0733 mol) and DMSO (50 ml). Ammonia gas (2 g, 0.118 mol, 1.6 equiv.) was added into the closed reactor and the mixture was heated under stirring to 145-150° C. to obtain a pressure sustaining a glass reactor of about 5 bars. After heating at 140-150° C. for 10 hours the pressure was reduced to atmospheric pressure and the reaction mixture was cooled to ambient temperature. A sample was withdrawn and injected to an HPLC system. According to the HPLC chromatogram the product contained 51% of imiquimod and 49% of the compound II in the reaction mixture.

Then, a second portion of ammonia gas (2 g) was added into the closed reactor at ambient temperature followed by heating the reaction mixture to 145° C. to obtain a pressure of about 5 bar. The heating was continued for 12 hours during which time the pressure was reduced to 2.5 bar. The reaction mixture was cooled to ambient temperature and a sample was withdrawn and injected to an HPLC system. According to the HPLC chromatogram the product contained 99.93% of imiquimod and 0.07% of compound II in the reaction mixture.

EXAMPLE 2

This example demonstrates the preparation of imiquimod by reaction of compound II with ammonia in DMSO at 140-150° C. under a pressure of about 5 bar.

A 250 glass reactor "Miniclave" was charged with 4-chloro-1-isobutyl-1H-imidazo [4,5-c]quinoline (II) (20 g, 0.0733 mol) and DMSO (50 ml). Ammonia gas (2 g, 0.118 mol, 1.6 equiv.) was added into the closed reactor and the mixture was heated under stirring to 145-150° C. to obtain a pressure sustaining a glass reactor of about 5 bars. After heating at 140-150° C. for 10 hours the pressure was reduced to atmospheric pressure and the reaction mixture was cooled to ambient temperature.

Then, a second portion of ammonia gas (2 g) was added into the closed reactor at ambient temperature followed by heating the reaction mixture to 145° C. to obtain a pressure of about 5 bar. The heating was continued for 6 hours during which time the pressure was reduced to 2.5 bar. The reaction mixture was cooled to ambient temperature and a sample was withdrawn and injected to an HPLC system. According to the HPLC chromatogram the product contained about 92% of imiquimod and 8% of compound II in the reaction mixture.

A colorless precipitate was collected by filtration and washed with water (3×50 ml). The wet product was treated with water (80 ml) under stirring at 70-80° C. for 1 hour. Then, the hot suspension was filtered and the precipitate was washed with hot water (40 ml) and methanol (40 ml) and dried at 80° C. under reduced pressure to yield 16.0 g of crude imiquimod in 85.7% yield; having a purity of 99.9% (by HPLC).

EXAMPLE 3

This example demonstrates the purification of imiquimod by slurrying crude imiquimod, containing 8% of 4-chloro-1-isobutyl-1H-imidazo[4,5-c]quinoline, in methanol.

A suspension of crude imiquimod (2 g, containing 8% of 4-chloro-1-isobutyl-1H-imidazo[4,5-c] quinoline) in methanol (14 ml) was stirred under reflux for 4 hours. The hot mixture was then filtered off and the obtained solid was washed with methanol and dried at 60° C. overnight to afford 1.9 g of pure imiquimod in 95% yield, having 99.89% purity (by HPLC).

EXAMPLES 4-11

These examples demonstrate the purity of imiquimod obtained by slurrying crude imiquimod (having about 92% purity, by HPLC) in various organic solvents in a similar procedure to the one detailed in example 3. The results are listed in Table 1.

TABLE 1

| Example Number | Crude imiquimod (g) | Solvent | Solvent vol. (mL) | Purity of imiquimod (%) | Yield (%) |
|---|---|---|---|---|---|
| 4 | 2 | 1-propanol | 7 | 99.94 | 80 |
| 5 | 3 | 2-propanol | 7 | 99.79 | 94.3 |
| 6 | 2 | Toluene | 7 | 99.86 | 95 |
| 7 | 2 | Acetonitrile | 7 | 99.93 | 90 |
| 8 | 2 | Acetone | 7 | 99.93 | 90 |
| 9 | 2 | Ethyl acetate | 7 | 99.80 | 90 |
| 10 | 2 | Tetrahydrofuran | 7 | 99.95 | 93.5 |
| 11 | 2 | 2-methyl-tetrahydrofuran | 7 | 99.86 | 91 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing 4-amino-1-isobutyl-1H-imidazo[4,5-c]quinoline of formula (I) (imiquimod):

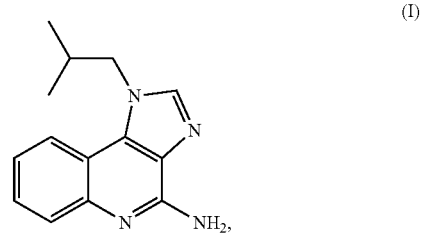

the process comprising:
heating a mixture comprising 4-chloro-1-isobutyl-1H-imidazo[4,5-c]-quinoline of formula (II):

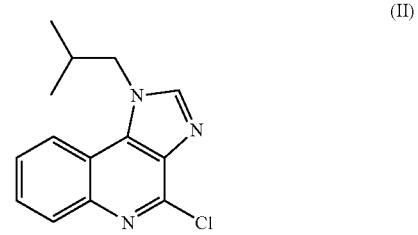

and ammonia in a polar, aprotic solvent, which is dimethyl sulfoxide (DMSO), N-methyl-2-pyrrolidone (NMP), tetramethylene sulfone (sulfolane), hexamethylphosphorotriamide (HMPA), or a mixture thereof, at relatively moderate pressure, to produce the compound of formula (I);
cooling the reaction mixture;
isolating the compound of formula (I); and
optionally purifying the compound of formula (I).

2. The process of claim 1, wherein the solvent is dimethyl sulfoxide (DMSO).

3. The process of claim 1, wherein the pressure is at most about 5 bars.

4. The process of claim 1, wherein the mixture comprises at least about 2 equivalents of ammonia relative to one equivalent of formula (II), and is heated at a temperature in the range of from about 140° C. to about 150° C.

5. The process of claim 1, comprising cooling the reaction mixture after reaction completion to precipitate imiquimod, isolating the imiquimod precipitate by filtration, and washing the precipitate.

6. The process of claim 5, wherein the precipitate is washed with water, methanol, ethanol, 1-propanol, 2-propanol, or a mixture thereof.

7. The process of claim 6, wherein the precipitate is washed with water, methanol or a mixture thereof.

8. The process of claim 1, wherein the crude imiquimod is obtained in greater than 85% yield.

9. The process of claim 1, wherein imiquimod is isolated from the reaction mixture and purified by precipitation, crystallization, slurrying, washing in a suitable solvent, filtration through a packed-bed column, dissolution in an appropriate solvent and re-precipitation by addition of a second solvent in which the compound is insoluble, or any combination of such purification methods.

10. The method of claim 9, wherein the compound of formula (I) is purified by a method comprising:
suspending the crude imiquimod in a slurrying solvent;
mixing the suspension, optionally at elevated temperature, to dissolve at least a portion of the imiquimod;
optionally filtering the solution;
cooling to produce crystals of imiquimod;
collecting the crystals by filtration; and
optionally washing and drying the crystals.

11. The method of claim 10, wherein the slurrying solvent comprises 1-propanol, 2-propanol, toluene, acetonitrile, acetone, ethyl acetate, tetrahydrofuran (THF), 2-methyltera-hydrofuran, or a mixture thereof.

12. The method of claim 11, wherein the solvent used for washing the crystals comprises water, methanol, ethanol, 1-propanol, 2-propanol, and mixtures thereof.

13. The method of claim 12, wherein the solvent used for washing the crystals is methanol.

14. The method of claim 10, wherein the imiquimod: slurrying solvent ratio is at least 2 g:2 ml (imiquimod: slurrying solvent).

15. The method of claim 14, wherein the imiquimod: slurrying solvent ratio is about 2 g:3-30 ml (imiquimod: slurrying solvent).

16. The process of claim 1, wherein the 4-amino-1-isobutyl-1H-imidazo[4,5-c]quinoline (imiquimod) (I) is obtained in a purity of at least about 98.5%.

17. The method of claim 16, wherein the 4-amino-1-isobutyl-1H-imidazo[4,5-c]quinoline (imiquimod) (I) is obtained in a purity of at least about 99.5%.

18. The method of claim 17, wherein the 4-amino-1-isobutyl-1H-imidazo[4,5-c]quinoline (imiquimod) (I) is obtained in a purity of at least about 99.8%.

* * * * *